US012599372B1

(12) United States Patent
Mitchell et al.

(10) Patent No.: US 12,599,372 B1
(45) Date of Patent: Apr. 14, 2026

(54) LUMBAR PUNCTURE LOCATOR DEVICE

(71) Applicants: Amber Mitchell, Kingston, NY (US);
Ralph Mitchell, Kingston, NY (US)

(72) Inventors: Amber Mitchell, Kingston, NY (US);
Ralph Mitchell, Kingston, NY (US)

( * ) Notice: Subject to any disclaimer, the term of this
patent is extended or adjusted under 35
U.S.C. 154(b) by 0 days.

(21) Appl. No.: 18/756,546

(22) Filed: Jun. 27, 2024

(51) Int. Cl.
| *A61B 10/00* | (2006.01) |
| *A61B 17/00* | (2006.01) |
| *A61B 17/34* | (2006.01) |

(52) U.S. Cl.
CPC ...... *A61B 10/0045* (2013.01); *A61B 17/3401*
(2013.01); *A61B 17/3403* (2013.01); *A61B*
*2010/0077* (2013.01); *A61B 2017/00128*
(2013.01); *A61B 2017/3413* (2013.01)

(58) Field of Classification Search
None
See application file for complete search history.

(56) References Cited

U.S. PATENT DOCUMENTS

| 8,920,388 B2 | 12/2014 | Slocum et al. |
| 9,597,054 B2 | 3/2017 | Kudavelly et al. |
| 10,980,567 B2 | 4/2021 | Sahhar |
| 2014/0288427 A1* | 9/2014 | Wall ..................... A61B 5/4566 |
| | | 600/439 |
| 2019/0117187 A1* | 4/2019 | Patel ................... A61B 8/4483 |
| 2019/0192114 A1* | 6/2019 | Mauldin, Jr. .......... A61B 8/085 |

* cited by examiner

*Primary Examiner* — Keith M Raymond
*Assistant Examiner* — Ashish S. Jasani
(74) *Attorney, Agent, or Firm* — Saile Ackerman LLC;
Stephen B. Ackerman

(57) ABSTRACT

This disclosure provides a device and a method for combining a lumbar puncture needle and an ultrasonic density detection circuitry to provide an inexpensive and accurate lumbar puncture locator device. The disclosed device senses different tissue densities with different frequency tones and colored light indicators before needle insertion in the patient's lumbar vertebrae region. This invention allows a doctor, a nurse practitioner or a physician assistant to safely do a lumbar puncture in an office environment without the scheduling of the use of the radiology department. This device will allow a timelier diagnosis of infections (such as Lyme disease, bacterial and viral meningitis, herpes, West Nile virus, syphilis), multiple sclerosis, Alzheimer's dementia, tumors, idiopathic intracranial hypertension, subarachnoid hemorrhage, and others.

15 Claims, 9 Drawing Sheets

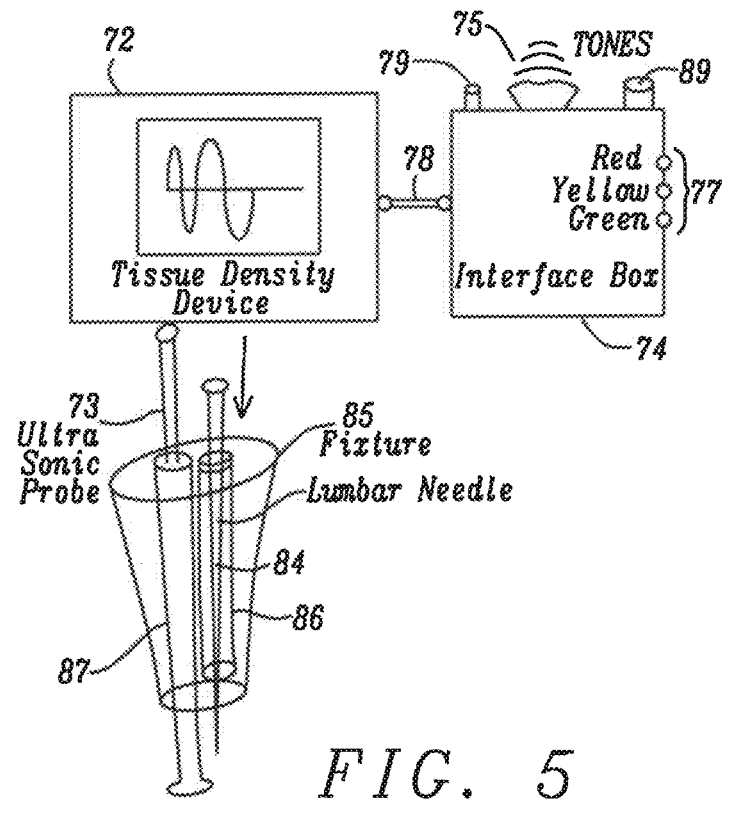
*FIG. 5*
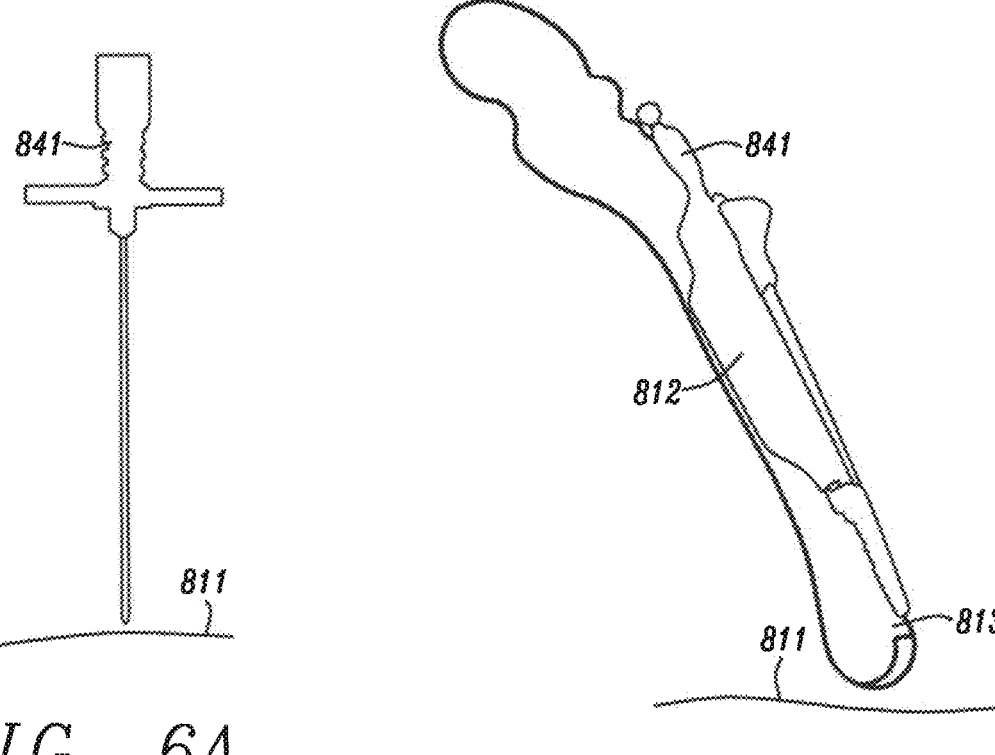
*FIG. 6A*                      *FIG. 6B*

*Direct Bone Hit*
*(Low Frequency Tone)*
*[Red Light]*

*Ligament, then*
*Bone Hit...No Clear*
*Path to CSF Spinal Fluid*
*(Medium Frequency Tone)*
*[Yellow Light]*

*Ligament Reflection*
*with Clear Path to*
*CSF Spinal Fluid*
*(High Frequency Tone)*
*[Green Light]*

LUMBAR PUNCTURE LOCATOR DEVICE

FIELD

This disclosure relates to a device and a method for lumbar puncture location of a bone-free path to CSF (cranial spinal fluid) and more particularly to the use of tissue density detection for accurate puncture insertion.

BACKGROUND

Currently lumbar punctures are done in one of two ways. The first way is for the doctor or other practitioner to insert an 18-20-gauge spinal needle into the L3/L4 (or L4/L5) disc space of the patient's spine using rough and blind knowledge of vertebrae anatomy. The objective is to locate a bone-free path to be able to extract CSF lumbar fluid for disease analysis. The drawbacks of this first method are the use of blind insertion of the needle, which often hurts the patient. The pain is caused by hitting bone instead of soft tissue, or hitting tissue inflamed by arthritis. Hitting bone or arthritic tissue leads to re-insertion attempts in order to hit required soft tissue and fluid. This trial-and-error method is time-consuming and painful for the patient. This trial-and-error method is usually done in the hospital due to potential complications of blind taps, such as back pain, post LP (lumbar puncture) headache, cerebral fluid leak requiring intervention, and blood patch. Another complication for the trial-and-error insertion method is that some patients have deformed back vertebrae due to scoliosis. Curved vertebrae are a challenge for trial-and-error needle insertion. Also, if a patient is obese, and the added fatty tissue around the spine further complicates spinal needle puncture locating.

The second, more expensive, alternative lumbar puncture method is X-ray guided puncture in a hospital radiology department. This is expensive and cannot be done in Emergency Rooms but requires a specialized radiology lab.

The fact that the use of the lumbar puncture procedure is not readily available for use in an emergency department, or a doctor's office, creates a serious diagnosis limitation. The following conditions and diseases could benefit from an office lumbar puncture: infections (such as Lyme disease, bacterial and viral meningitis, herpes, West Nile virus, syphilis), multiple sclerosis, Alzheimer's dementia, tumors, idiopathic intracranial hypertension, subarachnoid hemorrhage, and others. Without a readily available office lumbar puncture, many of these conditions and diseases will be misdiagnosed and mistreated, resulting in incorrect or delayed diagnosis.

SUMMARY

It is an objective of this disclosure to obtain pain-free, low-cost accurate lumbar punctures in a doctor's office or emergency room.

It is another objective of this disclosure to provide a device and a method for the use of tissue density detection for accurate lumbar puncture insertion into a patient's vertebrae area of the back.

The objects of this disclosure are achieved by the use of an LP (Lumbar Puncture) spinal needle combined with ultrasonic density detection circuitry.

The objects are further achieved by a device, which senses different tissue types using their density differences. The device emits audible tones of varying frequency and colored lights as the ultrasonic probe hovers over the skin of the patient's back before needle insertion. When the sound and light color associated with soft tissue are emitted, the doctor can insert the lumbar needle knowing that the needle will encounter soft tissue and fluid instead of hard tissue or bone.

The objects are further achieved by a device for accurately locating a soft tissue lumbar puncture location between vertebrae comprising:

a fixture which holds both a lumbar fluid extraction needle and an ultrasonic probe;

an interface device connected to said ultrasonic probe, configured to receive an output of said ultrasonic probe and convert said output to auditory and/or visual indicators of human bone and tissue.

The disclosed device prevents moving the lumbar needle into bone. The device guides a doctor or operator to only insert the lumbar needle when a non-bone direct path to the CSF fluid is identified. The device provides pain-free accuracy without the expense of a costly radiologic scheduled procedure.

The disclosed device further allows the lumbar puncture to be done outside of a hospital setting, since there are few side effects from pain and no blood or liquid leakage from incorrect punctures. Hence, a lumbar puncture procedure using the disclosed device is portable, inexpensive and can be done in a doctor's office.

BRIEF DESCRIPTION OF THE DRAWINGS

FIG. 5 presents a first embodiment of the disclosure with an audio interface box and a fixture combining the probe and needle.

FIG. 6A shows a standard lumbar needle of the related art.

FIG. 6B shows a combination of an ultrasonic probe and a lumbar needle.

DESCRIPTION

Ultrasound is generally defined as sound at frequencies of 20 kilohertz or greater, which is above the audible range for human hearing. Ultrasound is used in the medical field primarily for diagnostic medical imaging, to enable a medical professional or technician to see in real time, on an output device such as a display, internal structures such as muscles, tendons, organs, and bone. Frequencies of 1-20 megahertz are commonly used. The technology is relatively inexpensive, especially in comparison to other imaging techniques such as magnetic resonance imaging (MRI) and computed tomography (CT), and typically is portable.

Outside the medical field, ultrasound is used in ultrasonic testing, which is a form of nondestructive testing which can be utilized to detect flaws in materials and/or to measure objects' thickness. Frequencies of 2 to 10 megahertz are often used. The ultrasonic waves are produced through a transducer, and a reflected wave shown on an electronic display. In one application, a flaw or void will provide a different displayed signal than that displayed for material without the flaw.

Figures 3A, 3B, 4A, 4B:
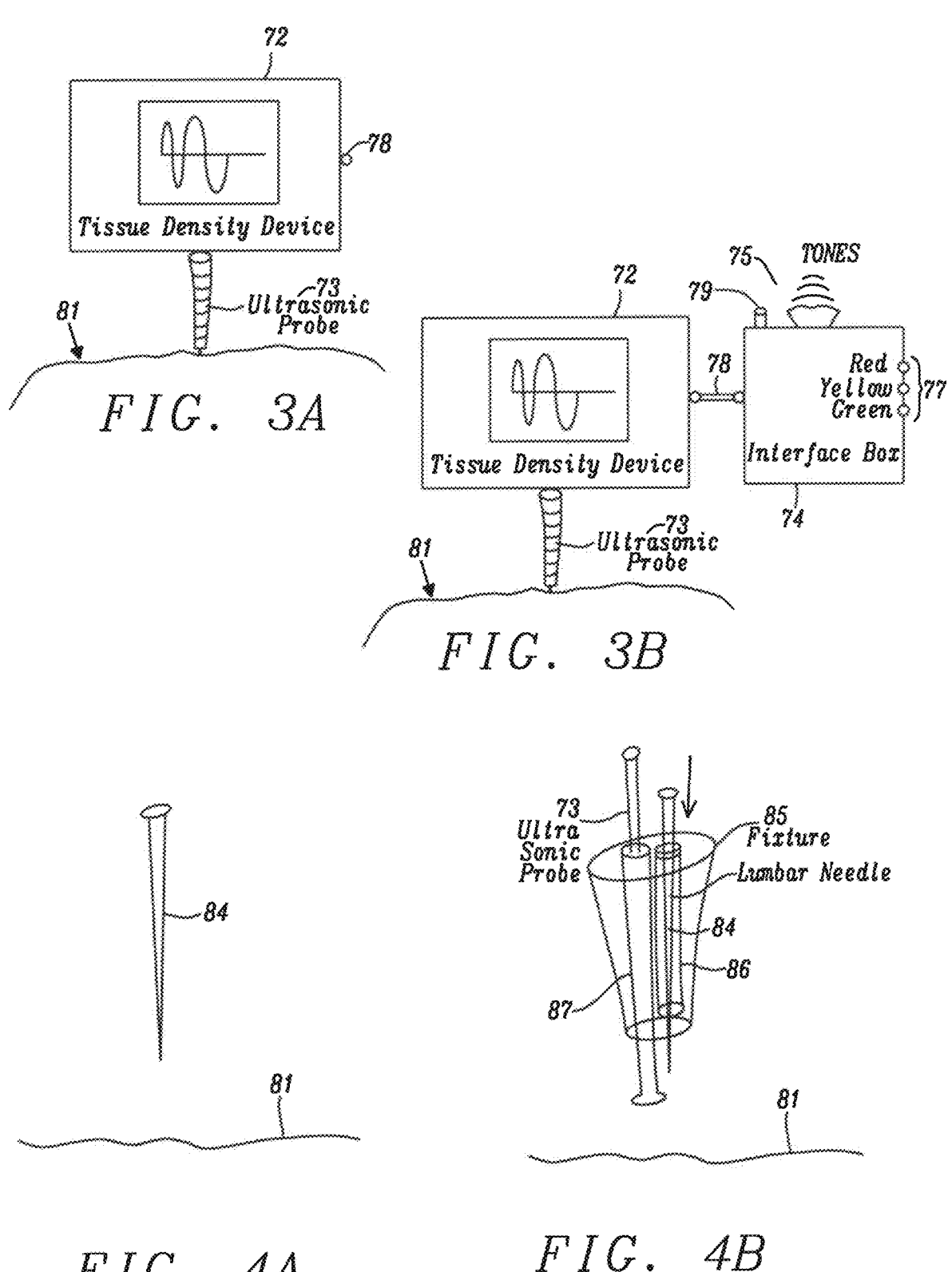
FIG. 3A shows a tissue density detector device of the disclosure with an ultrasonic probe hovering over the external skin of a patient's lumbar region.
FIG. 3B shows a tissue density detector device of the disclosure attached to an interface box with audio and colored light output.
FIG. 4A is a standard lumbar needle hovering over a patient's lumbar region.
FIG. 4B shows a fixture of the disclosure which combines lumbar needle and an ultrasonic probe hovering over the external skin of a patient's lumbar region.

The ultrasonic density detector of the disclosure, as shown in FIG. 3A, is of the type used in ultrasonic testing, in which simple signals are displayed, as opposed to the more complex display of an image as used in most medical ultrasound. An example of an ultrasonic flaw detector that could be utilized as a basis for the lumbar puncture locator device of the disclosure is the SADT (Sino Age Development Technology, Beijing, China) Flaw Detector-Model SUD 50.

Ultrasonic devices are typically operated in one of four modes.

1) A-mode (one-dimensional amplitude mode)—The transducer voltage recorded as a function of an inbound ultrasonic pulse and its rebounding outbound pulse. 2) B-mode (two-dimensional brightness mode)—An array of transducer element scans a plane through a body resulting in a two-dimensional image. 3) M-mode (motion mode)—This mode combines A-mode and B-mode. M-mode is voltage as a function of time. 4) D-mode (doppler mode)—Detect and measure moving targets, ie. Blood flow. The instant application an ultrasonic device operating in ultrasound A-mode.

Figure 1A:
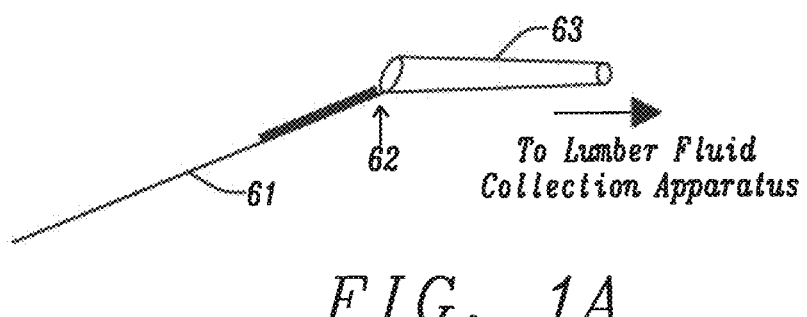
FIG. 1A is a prior art view of a standard lumbar puncture needle.

FIG. 1A is a side view of a standard Lumbar needle 61 of the related art, for extracting fluid from the spine of a patient. The device's opposite end 62 has an opening which empties the needle's extracted liquid to the Lumbar collection apparatus 63.

Figure 1B:
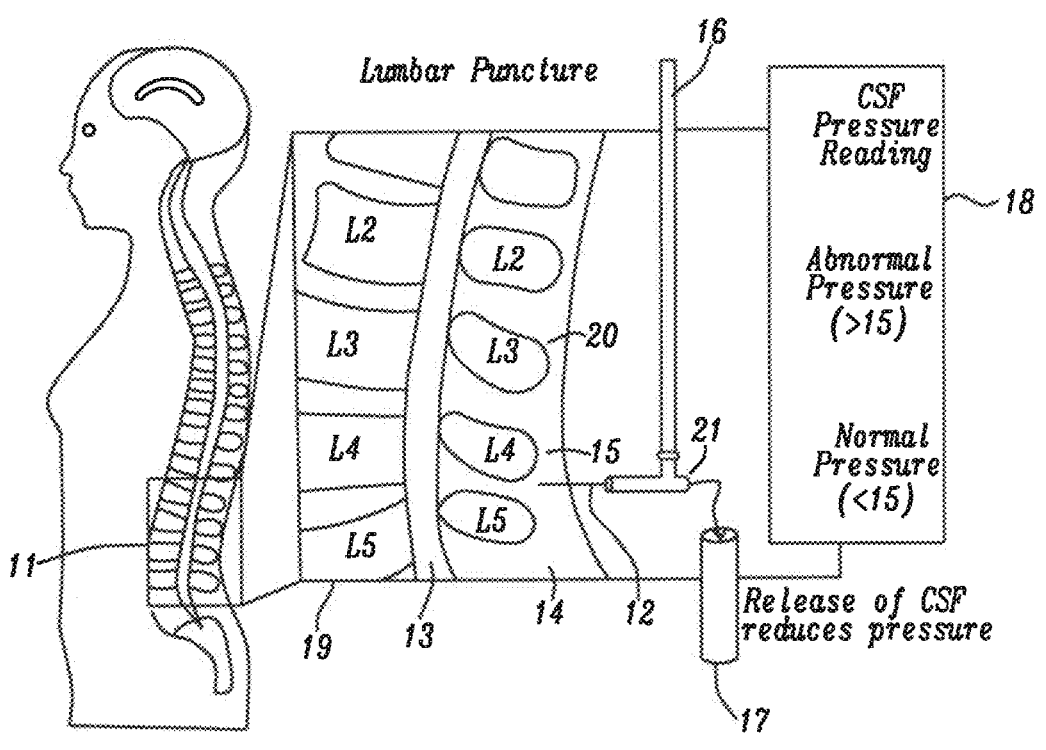
FIG. 1B is a side view of the lumbar (lower) region of a person's spinal column.

FIG. 1B is a side view of the lumbar (lower) region of a person's spinal column. A cross-section 11 of the spinal column is expanded 19 to show cerebrospinal fluid (CSF) 13 being extracted using a lumbar spinal needle 12. The lumbar spinal needle is shown protruding between the two spinal bones (L4, L5 circular vertebrae) 15 and 14. Alternatively, the lumbar spinal needle can be inserted between spinal bones (L3, L4 circular vertebrae) 20 and 15. FIG. 1B also shows a T-adapter 21 connected to the end of the lumbar needle 12. The top of the T-adapter is connected to a pressure-measuring manometer 16. The inset diagram 18 shows the normal pressure reading between 12 and 22 cm of H2O. Readings above 25 cm indicate elevated pressure due to possible tumor for example. Readings below 12 cm indicate low pressure and a possible spinal fluid leak. FIG. 1B also shows the CSF spinal fluid emptying into cylinder

17. Typically, the extracted lumbar fluid is sent to a lab for disease analysis and for additional diagnostic information.

Figure 1C:
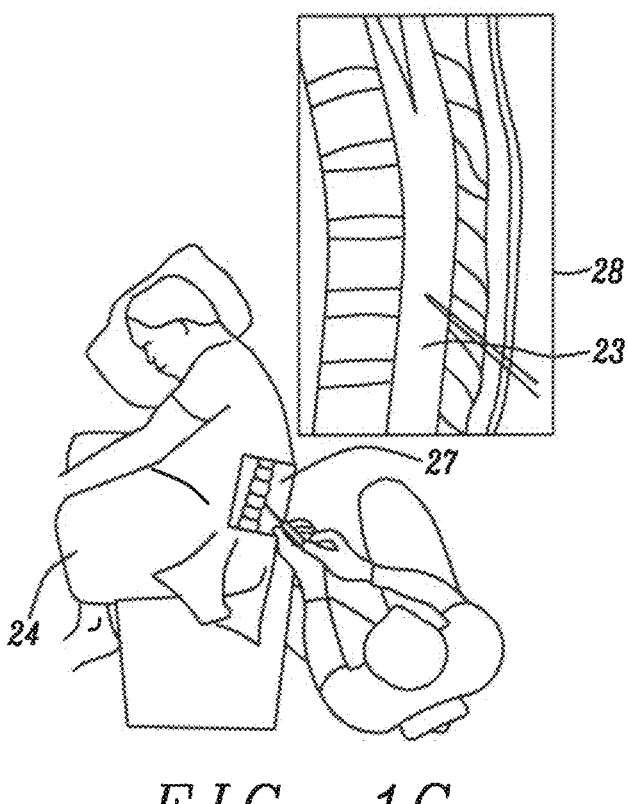
FIG. 1C is a top view of a patient receiving a lumbar puncture test.
Figure 1D:
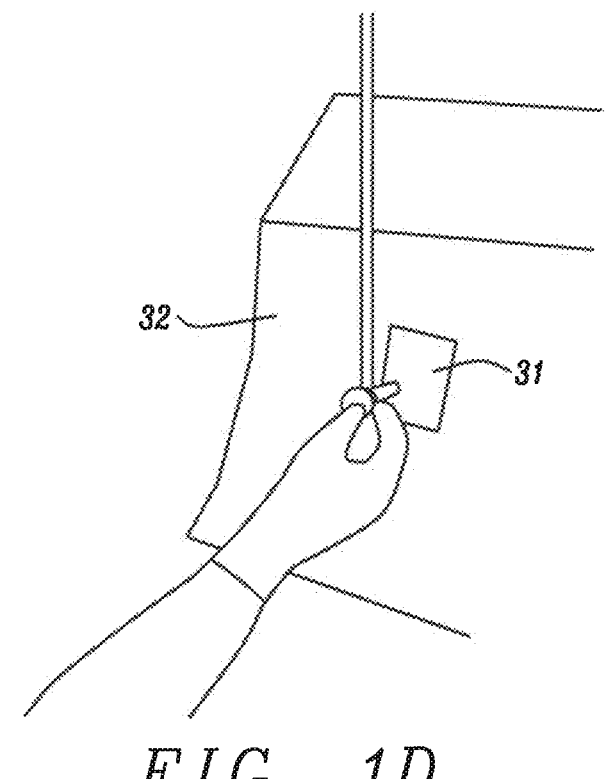
FIG. 1D is a rear view of a patient having a lumbar puncture.

FIG. 1C is a top view of a patient 24 receiving a lumbar puncture test. The needle puncture area 27 is shown in the inset 28. The lumbar needle 23 is inserted between the L4 and L5 vertebrae. FIG. 1D is a rear view of a patient having a lumbar puncture through an open square area 31 in a surgical covering 32.

Figure 1E:
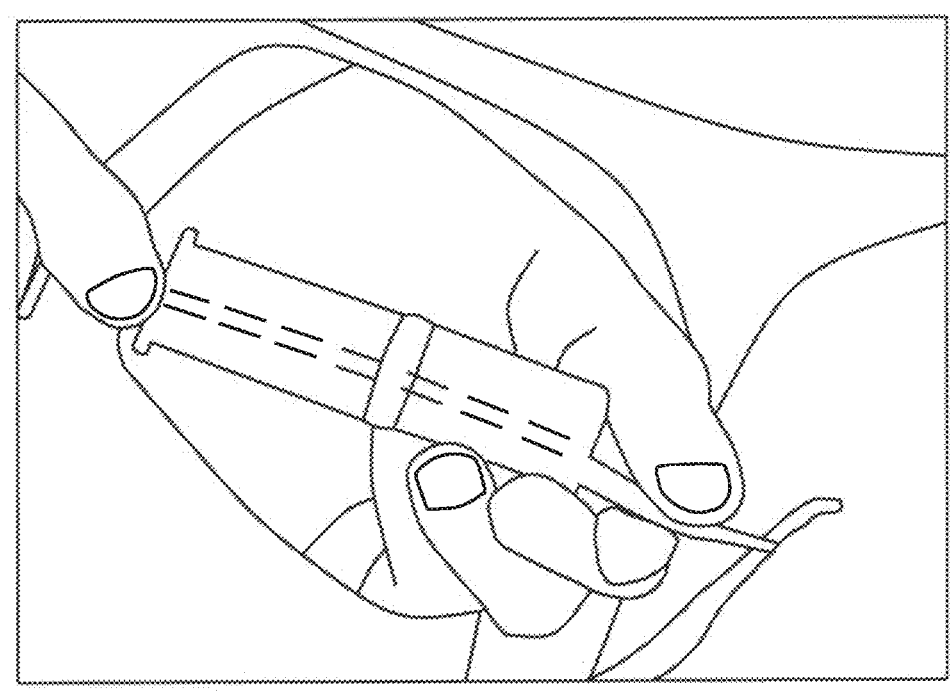
FIG. 1E is a close-up view of a lumbar puncture

FIG. 1E is a close-up view of how a doctor or operator currently inserts a lumbar needle into a patient's lumbar vertebrae through an open area in a surgical covering.

Figure 2:
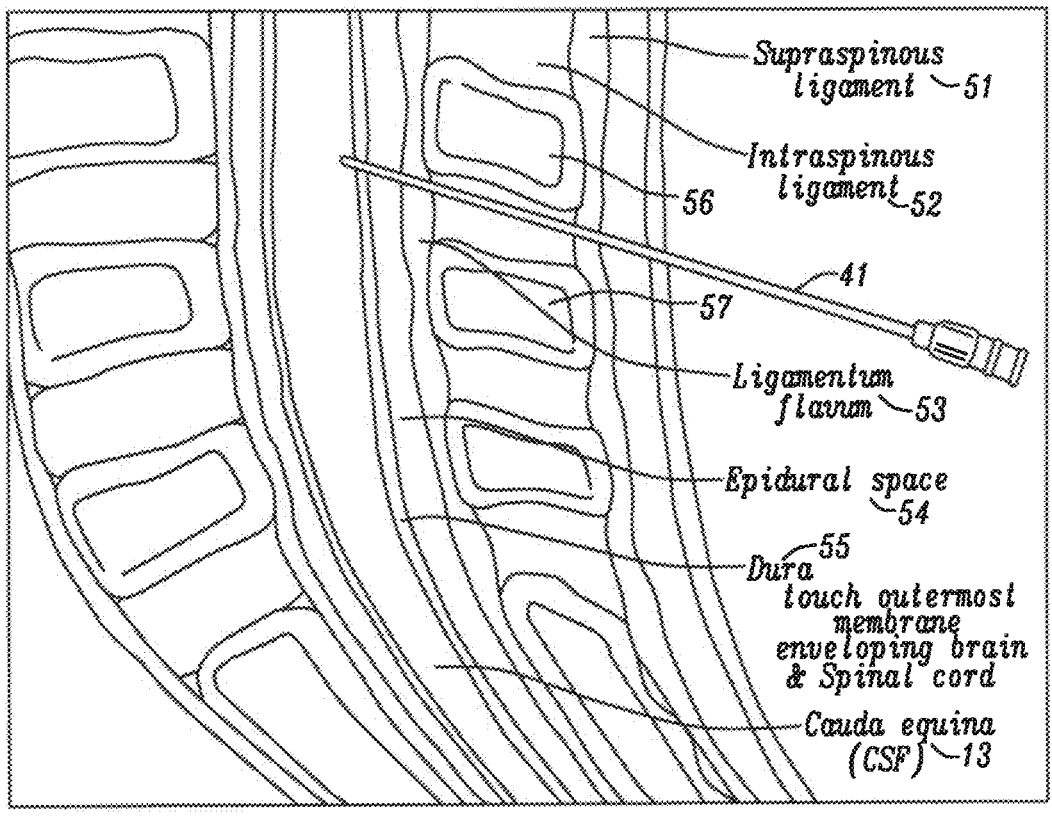
FIG. 2 is an enlarged side view of the cross-section shown in FIG. 1B.

FIG. 2 is an enlarged side view of the cross-section shown in FIG. 1B. A lumbar needle 41 is shown inserted between vertebrae L3 (56) and L4 (57). The lumbar needle is shown drawing cerebrospinal fluid (CSF) 13. FIG. 2 shows the different tissue material in the spinal column area. There are different tissues with different densities such as supraspinous ligament 51, Intraspinous ligament 52, Ligamentum flavum 53, Epidural space 54, and Dura 55.

The following figures will introduce and disclose two important elements of this disclosure: an ultrasonic density meter interface box, and an ultrasonic probe—lumbar needle fixture.

The ultrasonic density detector 72 of this disclosure is shown in FIG. 3A, and is used to distinguish human tissue types. The ultrasonic waves are transmitted to the surface of the patient's back 81 via an ultrasonic probe 73. The waves penetrate the vertebrae area. When the waves hit the interfaces within the patient's body, the waves will reflect, refract and be absorbed and attenuated. Since human tissues, such as bone, ligaments and fluid are different from one another, the amount of reflection, refraction, absorption and attenuation from each tissue type will be different. The ultrasonic density detector device 72 in FIG. 3A displays waveforms 70 on display 71 when the ultrasonic probe 73 hovers over bone tissue, versus ligament tissue, for example. In FIG. 3A, the device has an output signal 78, which corresponds to the tissue waveform displayed on the device screen. An example of the ultrasonic density detector in FIG. 3A is the SADT (Sino Age Development Technology, Beijing, China) Medical Flaw Detector device, SUD 50.

In FIG. 3B, the ultrasonic density meter output signal can be decoded by an interface box 74 disclosed in this application, to determine if tissue detected is bone, ligament or fluid based on an initial learning calibration performed on bone and muscle. Alternately, the interface box 74 could be integrated into a single enclosure with the detector 72. The interface box shown will emit a low frequency tone 75 when bone tissue is detected and will emit a medium frequency tone 75 when ligament and bone tissue is detected. The tones used to indicate the different tissue types could of course be varied (e.g., low for bone/ligament, medium for bone only, high frequency for no bone or ligament). In addition, there are colored lights 77 which are turned on to coordinate with the frequency tones. For example, a red light is turned ON when bone alone is detected. A yellow light is turned ON when ligament and bone are detected. A green light is turned ON when ligament alone is detected. The preceding colors could be varied. Also shown in FIG. 3B is an interface box activation switch 79, which is used to enable the operation of the interface box 74.

FIG. 4A shows the related art standard lumbar needle 84 hovering over a patient's external vertebrae skin 81. FIG. 4B shows a fixture 85, disclosed in this application. The fixture 85 combines a standard lumbar needle 84 and an ultrasonic probe 73. The fixture 85 is a cone-shaped receptable for both the removable lumbar needle 84 and the removable ultrasonic probe 73. Removable needles and probes allow for the use of different types of needles and probes. The cone-shape allows for easy insertion of the lumbar needle and ultrasonic probe while causing the needle and probe to be in close proximity at the opening of the cone at the patient's skin. The removable lumbar needle slides into a vertical cylinder 86 formed in the center of the fixture 85. This cylinder opens at the bottom of the cone-shaped fixture 85. The removable ultrasound probe slides into a second parallel cylinder 87, which also opens at the bottom of the cone-shaped fixture 85. FIG. 4B shows this fixture hovering over a patient's external vertebrae skin 81.

FIG. 5 illustrates a first embodiment of the disclosed device/system. FIG. 5 shows two new features of this disclosure, the interface box 74 and the fixture 85. The fixture is shown hovering over a patient's external vertebrae skin 81. The fixture contains a removable ultrasound probe 73, which is connected to the ultrasound density meter 72. The fixture also contains a removable lumbar needle 84, which is connected to the standard lumbar fluid collection tubes mentioned above in FIG. 1B. The interface box 74 is connected to the ultrasonic density meter 72 (or the box 74 and meter 72 could be integrated into a single structure) in order to produce low frequency tones 75 when the density probe and meter detects hard, bone tissue and to produce medium frequency tones 75 when the density probe and meter detects ligament soft tissue plus bone tissue. The doctor or operator would move the probe if either low frequency tones or medium frequency tones are heard. The doctor or operator would continue moving the probe until high frequency tones are heard. High frequency means that there is a direct path to the spinal fluid with no interference from bone tissue. (See FIG. 10C, hereinafter described). The doctor or operator would insert the lumbar needle at that skin location. The doctor or operator would continue inserting the lumbar needle as long as the high frequency tones continue. This continuation of high frequency tones indicates that spinal fluid has been encountered, since the high frequency tones have been calibrated to indicate that ultrasound reflections from spinal fluid are occurring. At that point, the doctor or operator would withdraw or extract the spinal fluid into the lumbar needle.

Sound and color lights calibration is done by forcing the detection of the two extremes of spinal fluid and bone. Calibration is performed by pointing the ultrasonic probe 73 at a known region 81 of spinal fluid in FIG. 5. Then, a sound adjustment knob 89 in the interface box 74 is moved until the highest frequency tone is emitted. When the interface box emits the highest frequency tone, the green light 77 is automatically activated. Similarly, in FIG. 5, calibration would continue by pointing the ultrasonic probe 73 at a known region 81 of bone. Then, the sound adjustment knob 89 on the interface box 74 is moved until the lowest frequency tone is emitted. When the interface box emits the lowest frequency tone, the red light 77 is automatically activated. After calibrating the two extremes of spinal fluid and bone, the mid-range case of detecting ligament then bone (see FIG. 10B) will result in the interface box 74 emitting a mid-range frequency tone and a yellow color light 77.

FIG. 6A shows a prior art standard lumbar needle 841 hovering over a patient's external vertebrae skin 811. FIG. 6B shows the standard lumbar needle 841 to be inserted into an ultrasonic probe holder 812, which has an adjacent slot for insertion of a needle. An exemplary fixture 812 for holding the needle 841 in close proximity to a probe 813 is the General Electric Needle Guide E8333JA (General Electric, Boston, Massachusetts), from General Electric Health-care. The probe holder 812 must keep the needle 841 in close proximity to the probe 813 in order to provide a very accurate tissue location for the lumbar needle insertion. This would need to be the case for the General Electric Needle Guide, since at least one application for its use is for the taking of biopsies in conjunction with real-time ultrasonic medical imaging. An ultrasound probe 813 capable of operating in the A mode would be used in probe holder 812, immediately adjacent to needle 841.

The GE Ultrasound Probe Transducer (EBC-RS) and the GE Needle Guide (E8333JA) are used in this disclosure to detect bone, muscle or spinal fluid and to retrieve spinal fluid. The above GE devices are typically used to take biopsies using real-time medical imaging.

Figure 7:
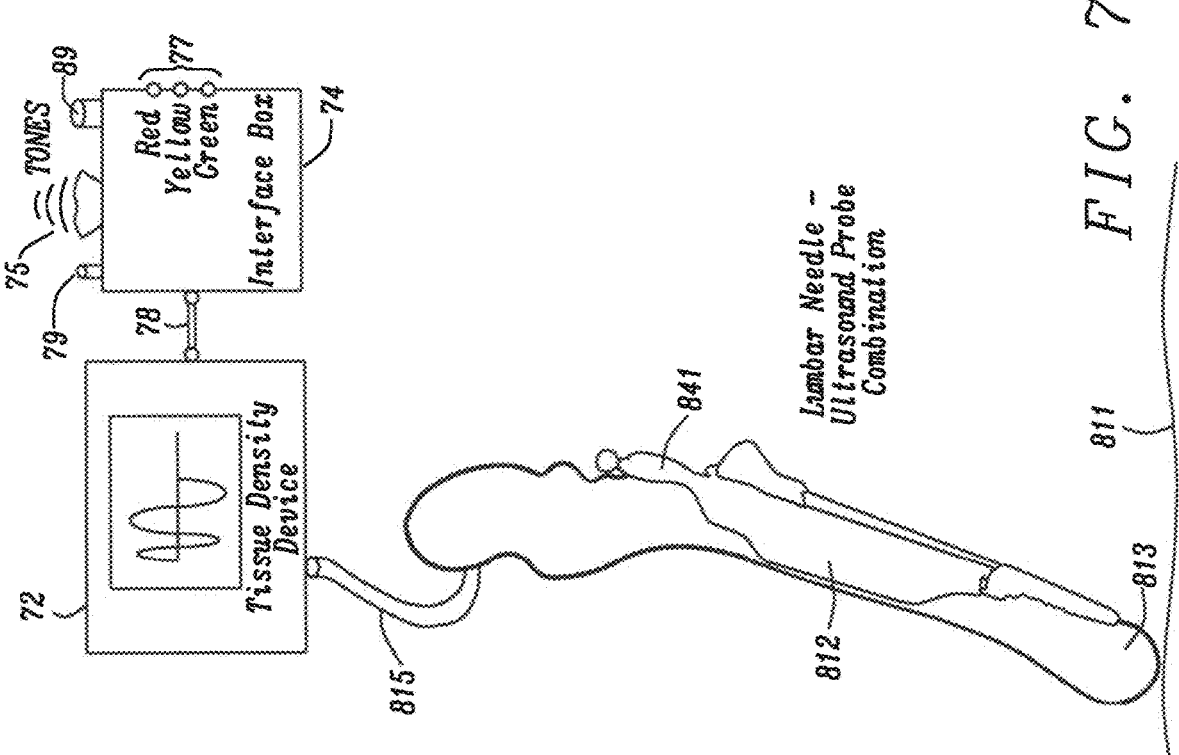
FIG. 7 presents a second embodiment of the disclosure with an audio interface box and ultrasonic probe combined with a lumbar needle.

FIG. 7 illustrates a second embodiment of the disclosure, combining the probe/needle combination of FIG. 6B with the previously discussed density device 72 and interface box 74. The probe/needle combination is shown hovering over a patient's skin 811, near the patient's vertebrae. The hollow ultrasonic probe 812 is connected to the ultrasound density meter 72 via an ultrasonic probe connection cable 815. The removable lumbar needle 841 is connected to standard lumbar fluid collection tubes mentioned above in FIG. 1B. The interface box 74 is connected to the ultrasonic density meter 72 in order to produce low frequency tones 75 when the density probe and meter detects hard, bone tissue and to produce medium frequency tones 75 when the density probe and meter detects ligament soft tissue plus bone tissue. The doctor or operator would move the probe if either low frequency tones or medium frequency tones are heard. The doctor or operator would continue moving the probe until high frequency tones are heard. High frequency means that there is a direct path to the spinal fluid with no interference from bone tissue. (See FIG. 10C) The doctor or operator would insert the lumbar needle at that skin location. The doctor or operator would continue inserting the lumbar needle as long as the high frequency tones continue. This continuation of high frequency tones indicates that spinal fluid has been encountered, since the high frequency tones have been calibrated to indicate that ultrasound reflections from spinal fluid are occurring. At that point, the doctor or operator would withdraw or extract the spinal fluid into the lumbar needle 841.

Figure 8:
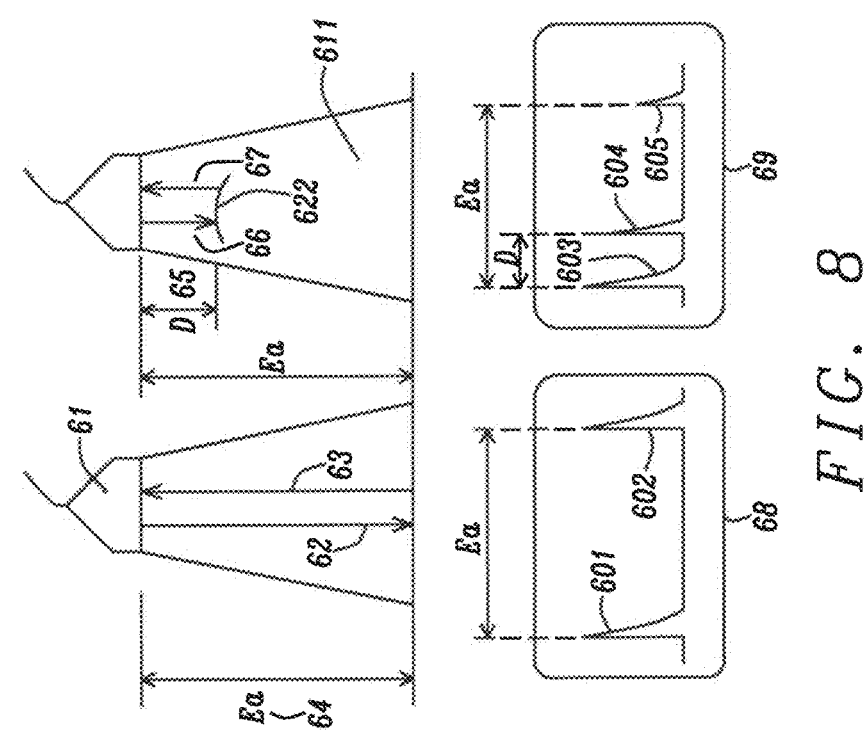
FIG. 8 presents ultrasonic density meter basic operation of the disclosure.

FIG. 8 illustrates the operating principle of the ultrasound density meter that detects and displays ultrasound signals, which are reflected from different substances at different distances. The results of these reflected signals are viewed on electronic displays 68 and 69.

An ultrasonic probe 61 sends out an ultrasonic signal 62. If the ultrasonic signal hits a hard substance such as bone 611, 100% of the energy of the transmitted ultrasonic signal will be reflected 63 back into the ultrasonic probe. On the ultrasound density meter display screen 68, the transmitted signal 601 and the reflected signal 602 are shown with equal energy amplitude and spaced by a distance of Ea. If the ultrasonic signal 66 hits, at a distance 65 from the suspended ultrasonic probe, a softer, less dense substance such as ligament 622, less than 100% of the energy of the transmitted ultrasonic signal will be reflected 67 back into the ultrasonic probe. On the ultrasound density meter display screen 69, the transmitted signal 603 and the reflected signals 604 (from ligament) and 605 (from the incident wave not reflected by ligament but reflected by bone tissue 611) are shown with diminished energy amplitudes and spaced by distances of D and Ea respectively.

The ultrasound density meter operating principle is based on the calibration of different ultrasonic wave reflection percentages based on the tissue type. The amplitude signals from the density meter screen shown in FIG. 8 indicate what type of tissues were encountered by the incident ultrasonic wave. The ultrasound density meter shown in FIG. 9 can be programmed to output a particular digital code, to indicate a finite set of tissue densities encountered. In the FIG. 9 embodiment, an Analog-to-Digital-Converter and processor 80 receive analog signals 701, 702, 703, etc. and convert them to a digital code, with the processor (typically, a microprocessor or microcontroller) being used to recognize the patterns for bone, ligament, etc. and output a corresponding digital signal 78.

Figure 9:
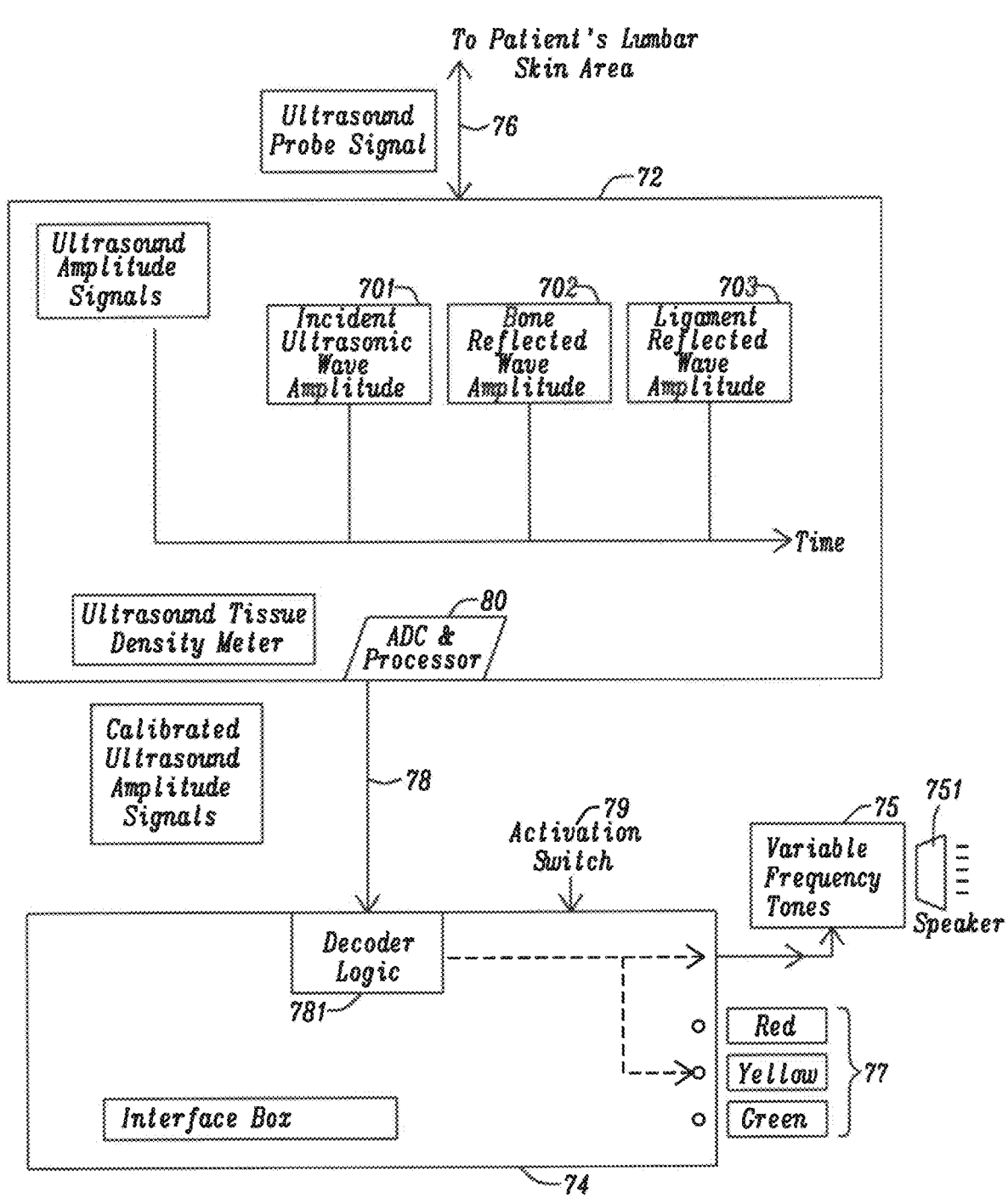
FIG. 9 presents density meter display and interface box connection of the disclosure.

FIG. 9 shows an example of the display screen of an ultrasound density meter 72. The ultrasonic probe 76 emits an incident ultrasonic wave, and the probe detects a reflection wave. The figure shows the density meter's display of the amplitude of the incident ultrasonic wave 701 and the reflected waves from bone 702 or from ligament 703. These detected amplitudes, which differentiate bone and ligament are converted into a calibrated signal output 78 from the ultrasound density meter 72.

The calibrated output signal 78 in FIG. 9 would present different pre-programmed codes to the decoder logic 781 to communicate the type of tissues detected by the density meter. The output signal 78 could present a code of 11, for example, to communicate that bone alone is detected in FIG. 10A. The output signal 78 could present a code of 12 to communicate that ligament and bone are detected in FIG. 10B. The output signal 78 could present a code of 13 to communicate that ligament alone is detected in FIG. 10C.

This amplitude signal 78 feeds into the Interface Box 74, which generates an audio tone at the speaker 751 based on the amplitude signal input. The audio tone generated is low frequency, for example, for bone alone encounters, is moderate frequency for ligament and bone encounters and is high frequency for ligament alone encounters. In addition, the amplitude signal feeds circuitry which illuminates either the red, yellow or green lights 77 on the interface box 74. The meaning of the 3 colors is as follows. The red color corresponds, for example, to the low frequency tone indicating bone alone in encountered. The yellow color light corresponds to the medium frequency tone indicating soft ligament tissue encountered. The green color light corresponds to the high frequency tone indicating spinal fluid alone encountered. The high frequency and green light tells the doctor or operator that there is a direct path to withdraw the CSF fluid. Providing both different frequency tones and colors gives doctors and operators two indicators which allow even more accurate lumbar locating efficiency.

Figures 10A, 10B, 10C:
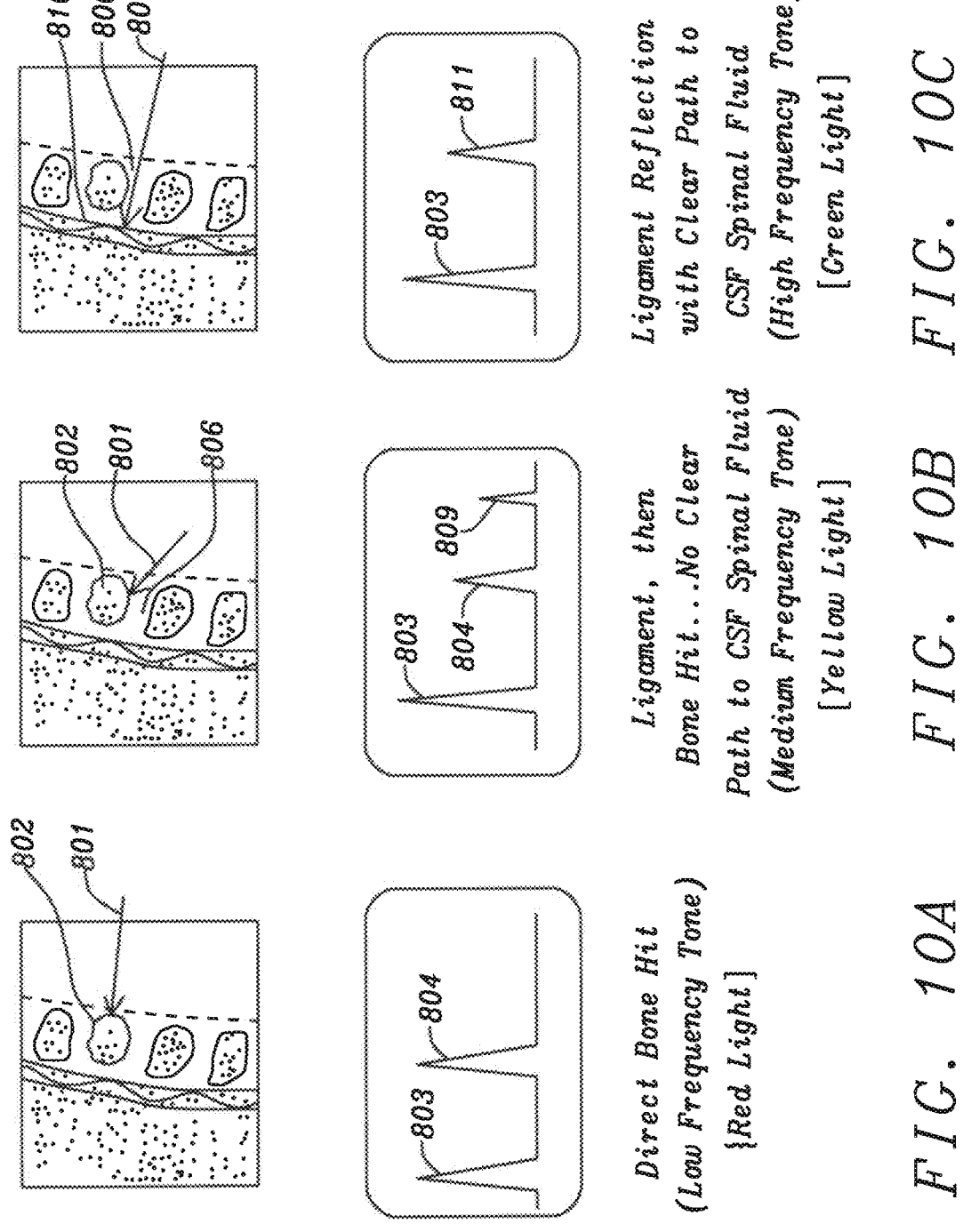
FIG. 10A shows an example of ultrasound direct bone hit.
FIG. 10B shows an example of ultrasound hitting ligament first followed by hitting bone.
FIG. 10C shows ultrasound direct path to cranial spinal fluid.

FIGS. 10A, 10B and 10C show the relationship among 4 items: the ultrasound probe signal position, the ultrasonic density meter display screen, the interface box different frequency output tones and the interface box colored panel lights.

FIG. 10A shows the ultrasonic probe signal 801 hitting vertebrae bone tissue 802. The density meter screen shows the incident ultrasound signal 803 and the 100% reflected wave 804. This display indicates a direct bone tissue "hit". As a result, the interface box receives the calibrated amplitude signal 78 in FIG. 7, indicating a direct bone "hit". This will produce a low frequency tone at the interface box output speaker 751. It will also produce the illumination of the Red light output on the interface box.

FIG. 10B shows the ultrasonic probe signal 801 hitting vertebrae ligament tissue 806 first, then hitting vertebrae bone tissue 802 second. The density meter screen shows the incident ultrasound signal 803 and the ligament reflected wave 808. In addition, the FIG. 10B display shows the bone tissue reflected wave 809. This display indicates ligament followed by bone "hits". As a result, the interface box receives the calibrated amplitude signal 78 in FIG. 7, indicating that there was not a clear, direct path to the spinal fluid. This will produce a medium frequency tone at the interface box output speaker 751. It will also produce the illumination of the Yellow light output on the interface box.

FIG. 10C shows the ultrasonic probe signal 801 hitting vertebrae ligament tissue 806 first, then hitting vertebrae spinal fluid 810 second. The density meter screen shows the incident ultrasound signal 803 and only the ligament reflected wave 811. Since there is no other reflected wave shown on the FIG. 10C meter screen, there must be a clear, direct path to the spinal fluid. As a result, the interface box receives the calibrated amplitude signal 78 in FIG. 7, indicating that there was clear, direct path to the spinal fluid. This will produce a high frequency tone at the interface box output speaker 751. It will also produce the illumination of the Green light output on the interface box.

Figure 11:
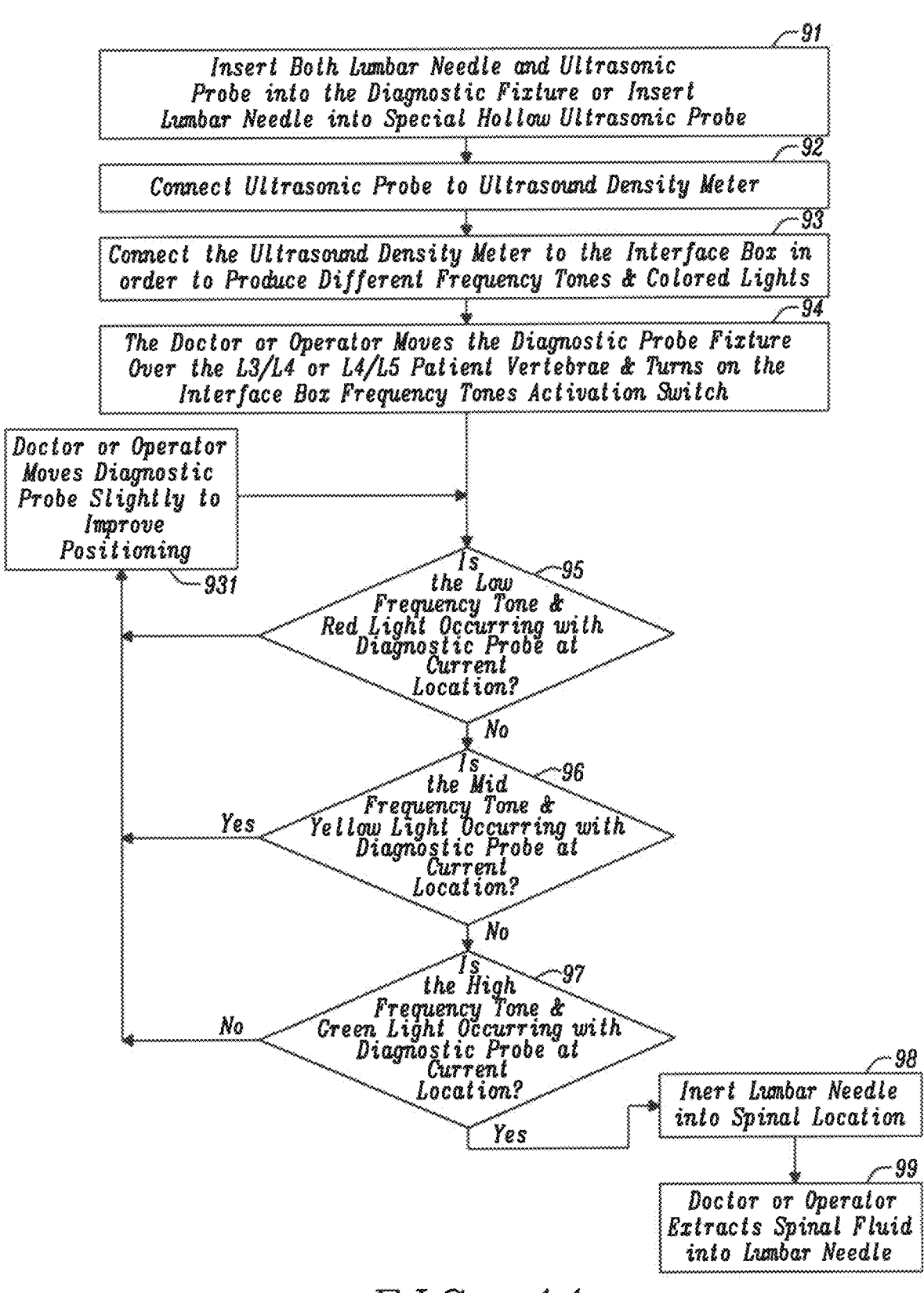
FIG. 11 is a lumbar puncture location device flowchart of the disclosure.

FIG. 11 is a flowchart of the Lumbar Puncture Locator method, which uses the Lumbar Puncture Locator Device. The Lumbar Puncture Locator Device is made up of two novel components, the Diagnostic Probe Fixture and the Interface Box. In block 91, there is the insertion of both the standard Lumbar needle and the ultrasonic probe into the Diagnostic Probe Fixture. Alternatively, there is the insertion of the standard lumbar needle into a hollow ultrasonic probe. Block 92 is the connecting of the ultrasonic probe to the ultrasound density meter. Block 93 is the connecting of the ultrasound density meter to the Interface Box in order to trigger different frequency tones and different colored lights as a function of the type of human tissue encountered by the ultrasound waves generated by the ultrasonic probe. In block 94, there is the moving of the ultrasonic probe over the skin surface of the patient's L3/L4 or L4/L5 vertebrae area. The decision block 95 asks if the operator hears a low frequency tone and sees a Red light lit on the front of the Interface Box associated with the probe directly detecting hard, bone tissue (as shown previously in FIG. 10A). If the answer is Yes, block 931 indicates that the doctor or operator moves the ultrasonic probe slightly to improve the chance of detecting soft tissue and lumbar fluid. If the answer is No, a second decision block 96 asks if the operator hears a mid-frequency tone and sees a Yellow light lit on the front of the Interface Box associated with the probe first detecting soft, ligament tissue, followed by encountering hard, bone tissue (as shown previously in FIG. 10B). If the block 96 answer is Yes, the operator repeats block 931 attempting to locate the spinal fluid area. If the block 96 answer is No, a third decision block 97 asks if the operator hears the high frequency tone and sees a Green light lit on the front of the Interface Box associated with the probe having an unobstructed, clear path to the spinal fluid (as shown previously in FIG. 10C). If the block 97 answer is Yes, the doctor inserts the lumbar needle into the target spinal location as in block 98 to extract spinal fluid into the Lumbar needle as shown in block 99. If the block 97 answer is No, the operator repeats block 931 attempting to locate the spinal fluid area.

FIG. 11 demonstrates that the instant invention allows a doctor, a nurse practitioner or a physician assistant to safely do a lumbar puncture in an office environment without the scheduling of the use of the radiology department. This device will allow a timelier diagnosis of infections (such as Lyme disease, bacterial and viral meningitis, herpes, West Nile virus, syphilis), multiple sclerosis, Alzheimer's dementia, tumors, idiopathic intracranial hypertension, subarachnoid hemorrhage, and others.

While this disclosure has been particularly shown and described with reference to the preferred embodiments thereof, it will be understood by those skilled in the art that various changes in form and details may be made without departing from the spirit and scope of this disclosure.

What is claimed is:

1. A device for accurately locating a soft tissue lumbar puncture location between vertebrae comprising:

a fixture which holds both a lumbar fluid extraction needle and an ultrasonic probe;

a tissue density meter which receives ultrasound signals from said ultrasonic probe, and in response outputs a digital code, which corresponds to at least one of bone or tissue;

an interface box housing:

an input for receiving said digital code, and combinatorial logic for converting said digital code to one or more auditory and/or visual indicators, wherein each unique indicator is associated with a unique digital code.

2. The device of claim 1 wherein said fixture has a $1^{st}$ slot for holding a removable lumbar fluid needle probe and a $2^{nd}$ slot for holding a removable ultrasonic probe, wherein said probe and said needle are in close proximity to each other.

3. The device of claim 1 wherein said fixture has a hollow opening wherein said lumbar fluid extraction needle can be inserted into said hollow opening, wherein said fixture has a cut-away which allows said ultrasonic probe and said fluid extraction needle to be in close proximity to each other.

4. The device of claim 1 wherein said interface device comprises a density meter and an output device, wherein said density meter generates a signal denoting density of tissue detected by said ultrasonic density probe.

5. The device of claim 4 wherein said output device utilizes said signal from said density meter to produce a specific audible sound assigned to a specific tissue type.

6. The device of claim 4 wherein said output device utilizes said signal from said density meter to illuminate a light of a specific color assigned to a specific tissue type.

7. The device of claim 5 wherein said interface device is configured to produce three distinctive sounds: low frequency for hard bone tissue, medium frequency for soft ligament tissue, and very high frequency for spinal fluid.

8. The device of claim 6 wherein said interface device is configured to illuminate a light of a specific color assigned to a specific tissue density: red light for hard bone tissue, yellow light for soft ligament tissue, and green light for spinal fluid.

9. A method of accurately locating a soft tissue lumbar puncture location between vertebrae comprising the steps of:

providing a fixture which holds both a lumbar fluid extraction needle and an ultrasonic probe;

providing a tissue density meter which receives ultrasound signals from said ultrasonic probe, and in response outputs a digital code, which corresponds to at least one of bone or tissue;

providing an interface box housing:

an input for receiving said digital code, and combinatorial logic for converting said digital code to one or more auditory and/or visual indicators, wherein each unique indicator is associated with a unique digital code; and moving said fixture over a patient's vertebrae-adjacent skin until said device outputs a visual or auditory signal indicating a soft tissue lumbar location has been established, allowing a doctor, nurse or technician to extract lumbar fluid at said soft tissue lumbar location, said lumber fluid is used to test for abnormalities and diseases.

10. The method of claim 9 further comprising inserting the lumbar fluid needle into a patient's vertebrae-area skin, between vertebrae, in order to extract lumbar fluid to be analyzed.

11. The method of claim 9 wherein said interface device comprises a density meter and an output device, wherein said density meter generates a signal denoting density of tissue detected by said ultrasonic density probe.

12. The method of claim 10 wherein said output device utilizes said signal from said density meter to produce a specific audible sound assigned to a specific tissue type.

13. The method of claim 10 wherein said output device utilizes said signal from said density meter to illuminate a light of a specific color assigned to a specific tissue type.

14. The method of claim 11 wherein if said interface device is configured to produce three distinctive sounds: low frequency for hard bone tissue, medium frequency for soft ligament tissue, and very high frequency for spinal fluid, wherein after moving said probe while detecting a low frequency bone sound until detecting the high frequency sound denoting a clear path to the spinal fluid region when the doctor or operator would puncture said vertebrae skin between the required vertebrae in order to insert said lumbar needle into the spinal fluid region in order to extract the required lumbar fluid for analysis.

15. The method of claim 12 wherein if said interface device is configured to illuminate a light of a specific color assigned to a specific tissue density: red light for hard bone tissue, yellow light for soft ligament tissue, and green light for spinal fluid, wherein after moving said probe while detecting the red light denoting bone until detecting the green light denoting a clear path to the spinal fluid region when the doctor or operator would puncture said vertebrae skin between the required vertebrae in order to insert said lumbar needle into the spinal fluid region in order to extract the required lumbar fluid.

* * * * *